(12) United States Patent
Naddaka et al.

(10) Patent No.: US 7,060,841 B2
(45) Date of Patent: Jun. 13, 2006

(54) PROCESS FOR PREPARING 1-METHYLINDAZOLE-3-CARBOXYLIC ACID

(75) Inventors: Vladimir Naddaka, Lod (IL); Shadi Saeed, Haifa (IL); Dionne Montviliski, Givataim (IL); Oded Arad, Rehovot (IL); Joseph Kaspi, Givatayim (IL)

(73) Assignee: Chemagis Ltd., Bnei Brak (IL)

( * ) Notice: Subject to any disclaimer, the term of this patent is extended or adjusted under 35 U.S.C. 154(b) by 315 days.

(21) Appl. No.: 10/453,427

(22) Filed: Jun. 3, 2003

(65) Prior Publication Data

US 2004/0248960 A1    Dec. 9, 2004

(51) Int. Cl.
    *C07D 231/56*    (2006.01)
(52) U.S. Cl. .................................. 548/362.5
(58) Field of Classification Search .............. 548/362.5
    See application file for complete search history.

(56) References Cited

U.S. PATENT DOCUMENTS

| 4,886,808 | A  | 12/1989 | King         |
| 5,034,398 | A  | 7/1991  | King         |
| 5,225,407 | A  | 7/1993  | Oakley et al.|
| 6,294,548 | B1 | 9/2001  | James        |

FOREIGN PATENT DOCUMENTS

| EP | 0200444 A2 | 11/1986 |
| EP | 0200444 B1 | 11/1992 |
| EP | 0323105 B1 | 10/1999 |

OTHER PUBLICATIONS

Addelman et al., "Phase I/II Trial of Granisetron: A Novel 5-Hydroxytryptamine Antagonist for the Prevention of Chemotherapy-Induced Nausea and Vomiting," *Journal of Clinical Oncology*, 8(2): 337-341 (1990).
Allen et al., "Pharmacokinetics and Tolerability of Ascending Intravenous Doses of Granisetron, a Novel 5-HT$_3$ Antagonist, in Healthy Human Subjects," *Eur. J. Clin. Pharmacol.*, 48: 159-162 (1994).
Allen et al., "The Pharmacokinetics of Granisetron, a 5-HT$_3$ Antagonist in Healthy Young and Elderly Volunteers," *Eur. J. Clin. Pharmacol.*, 48: 519-520 (1995).
Auwers et al., "Über Alkylderivative der Indazolcarbonsäure-(3)," *Chem. Ber.*, 52: 1340-1351 (1919).
Carmichael et al., "A Pharmacokinetic Study of Granisetron (BRL 43694A), a Selective 5-HT$_3$ Receptor Antagonist: Correlation with Anti-emetic Response," *Cancer Chemother. Pharmacol.*, 24: 45-49 (1989).
Cassidy et al., "Pharmacokinetics and Anit-emetic Efficacy of BRL43694, a New Selective 5HT-3 Antagonist," *Br. J. Cancer*, 58: 651-653 (1988).
Ettinger et al., "A Double-Blind Comparison of the Efficacy of Two Dose Regimens of Oral Granisetron in Preventing Acute Emesis in Patients Receiving Moderately Emetogenic Chemotherapy," *Cancer*, 78(1): 144-151 (1996).
Gordon et al., *The Chemist's Companion: a Handbook of Practical Data, Techniques, and References*, pp. 432-435 (John Wiley & Sons, Inc.; 1972).
*Remington: The Science and Practice of Pharmacy*, vol. II, 19$^{TH}$ Ed., Ch. 87, pp. 1526-1533 (Mack Publishing Co., 1995).
Rousseau et al., "Structure and Ultraviolet Absorption Spectra of Indazole, 3-Substituted Indazole and some of Their Derivatives," *Journal of the American Chemical Society*, 72(5): 3047-3051, 1950.

*Primary Examiner*—Kamal A. Saeed
(74) *Attorney, Agent, or Firm*—Leydig, Voit & Mayer, Ltd

(57) ABSTRACT

The invention provides a process for preparing 1-methylindazole-3-carboxylic acid of formula (I):

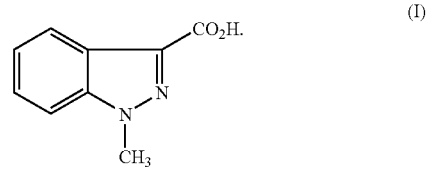

which comprises reacting a methylating agent with indazole-3-carboxylic acid of formula (VI):

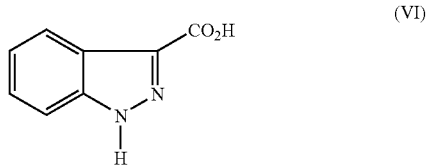

in the presence of an alkaline earth metal oxide or alkoxide in an appropriate solvent. Also provided is a process for producing Granisetron, using the method of the present invention for producing 1-methylindazole-3-carboxylic acid.

9 Claims, No Drawings

PROCESS FOR PREPARING 1-METHYLINDAZOLE-3-CARBOXYLIC ACID

BACKGROUND OF THE INVENTION

1. Field of the Invention

This invention relates to an improved process for preparing 1-methylindazole-3-carboxylic acid (1-MICA) of formula (I):

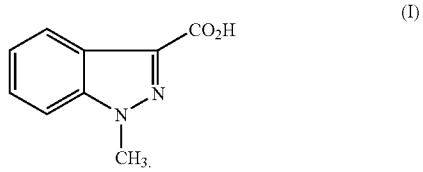

This invention also relates to the preparation of the antiemetic drug Granisetron {endo-1-Methyl-N-(9-methyl-9-azabicyclo[3.3.1]non-3-yl)-1H-indazole-3-carboxamide} and its hydrochloride salt, which drug is disclosed in EP 200,444 (Beecham Group), using the process of the present invention for preparing 1-MICA.

2. Description of the Related Art

The synthesis of 1-MICA has been described by K. v. Auwers and R. Dereser: Chem. Ber. 1919, 52, 1340–1351. This method involves methylation of the compound of formula (II) with iodomethane in methanol in the presence of sodium methoxide obtained in situ by reaction of sodium with methanol. 1-MICA is a known intermediate, which is useful for the production of the antiemetic drug Granisetron (endo-1-Methyl-N-(9-methyl-9-azabicyclo[3.3.1]non-3-yl)-1H-indazole-3-carboxamide) and its hydrochloride salt. See, e.g., EP 0200444.

A mixture of 1- and 2-isomers (compounds III and IV) with a domination of 1-isomer (III) is obtained in the procedure.

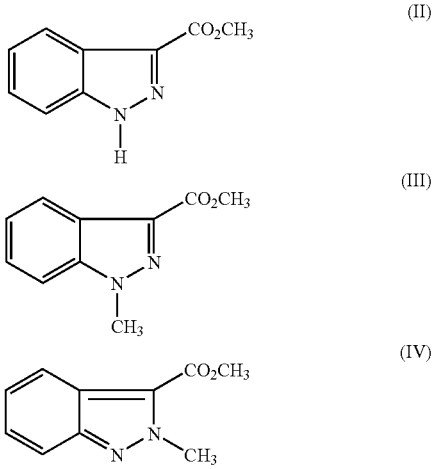

Crystallization of the mixture from petroleum ether gives a pure 1-isomer. 1-MICA is obtained by hydrolysis of methyl ester III. This is an undesirable route as it involves the use of sodium metal for the generation of sodium methoxide. The use of sodium metal in industrial scale is disadvantageous for safety reasons. In addition, the selectivity for 1-MICA in this process is only ca 2:1 (relative to 2-MICA), and the purification and hydrolysis steps result in low yields (ca 30%).

An alternative process involving methylation of the compound of formula (V) is described by V. Rousseau and H. G. Lindwall, JACS 1950, 72, 3047.

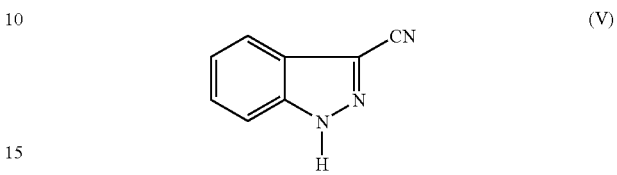

This process also results in a mixture of isomers and involves purification and hydrolysis steps.

A one stage highly selective process for producing 1-MICA has been described in EP 323, 105 (Beecham Group). The process comprises the reaction of a methylating agent with indazole-3-carboxylic acid (ICA) of formula (VI) in a polar solvent in which is dissolved an alkali metal alkoxide.

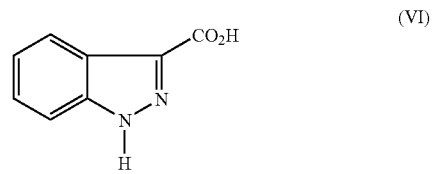

Preferable solvents are anhydrous lower alkanols. The alkali metal alkoxide is usually formed in situ by reaction of alkali metal with the lower alkanol solvent. 1-MICA is obtained in high yield. However, hydrogen evolves at in situ preparation of alkali metal alkoxide and it makes this process hazardous on an industrial scale preparation of 1-MICA. In addition, during the course of the reaction methyl esters of 1-MICA and 2-MICA are formed (ca. 10%). The reaction mixture obtained using this procedure contains at the end of reaction ca 7% 2-MICA.

SUMMARY OF THE INVENTION

This invention provides an improved process for preparing 1-MICA in high yield by a reaction of ICA with a methylating agent in a suitable solvent in the presence of an oxide or alkoxide of a metal of the alkaline earth group. The solvent does not have to be anhydrous.

According to the present invention 1-MICA can be obtained by this reaction with higher purity and without side-products (1-MICA ester, 2-MICA ester, and ICA ester).

According to the present invention 1-MICA can be obtained by this reaction without the in situ preparation of the alkoxide; and thus the process of this invention is substantially less hazardous. The alkaline earth metal oxides are readily available, inexpensive, and safe.

The present invention further provides a process for the preparation of the drug Granisetron (endo-1-Methyl-N-(9-methyl-9-azabicyclo[3.3.1]non-3-yl)-1H-indazole-3-carboxamide or N-(endo-9-methyl-9-azabicyclo[3.3.1]non-3-yl)-1-methylindazole-3-carboxamide) or a salt thereof using the process of the present invention for preparing 1-MICA.

Other objects and advantages of the present invention will be apparent from the following description.

DETAILED DESCRIPTION OF THE INVENTION

As used herein, the following abbreviations are used: 1-methylindazole-3-carboxylic acid (1-MICA); 2-methylindazole-3-carboxylic acid (2-MICA); indazole-3-carboxylic acid (ICA); 1-methylindazole-3-carboxylic acid methyl ester (1-MICA ester); 2-methylindazole-3-carboxylic acid methyl ester (2-MICA ester); indazole-3-carboxylic acid methyl ester (ICA ester).

More specifically the present invention provides the improved process for preparing 1-MICA of formula (I), which comprises the reaction of a methylating agent with ICA of formula (VI) in an appropriate solvent in the presence of an oxide or alkoxide of alkaline earth metal. The transformation from starting material to product involves a highly selective N-methylation in position 1 as depicted in Scheme 1.

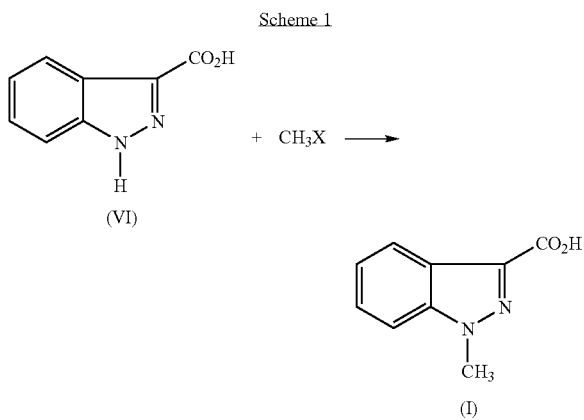

Oxides and alkoxides of the metals of the alkaline earth group are commercially available, low cost bases. These compounds are effective desiccants and are used extensively for drying organic solvents (A. J. Gordon and R. A. Ford, The Chemist's Companion: a handbook of practical data, techniques, and references, Copyright by John Wiley & Sons, Inc., 1972, p.p. 432–435).

While Applicants do not wish to be bound by any particular theory, it is believed that the reaction occurs by initial formation of the $N^-$ and $COO^-$ dianion of ICA with the oxide or alkoxide of the alkaline earth metal. The dianion then converts to 1-MICA with the methylating agent.

One molar equivalent of the oxide or alkoxide of the alkaline earth metal is required for preparing the dianion of ICA.

Preferably, more than one molar equivalent of the oxide or alkoxide relative to ICA is used in the process.

More preferably, two molar equivalents of the oxide or alkoxide relative to ICA are used in the process.

Oxides and alkoxide of magnesium, calcium, strontium and barium may be used in the process and preferably the oxide of the alkaline earth metal is selected from the group consisting of calcium oxide, barium oxide, and magnesium oxide.

Suitable examples of the methylating agent include iodomethane, bromomethane, dimethyl sulfate, and trimethyl phosphate or another compound of formula $CH_3X$ wherein X is a leaving group, such as mesylate or tosylate. An excess of the methylating agent is beneficial to the reaction. Preferably about two molar equivalents of the methylating agent relative to ICA are usually used, and preferably the methylating agent is selected from the group consisting of dimethyl sulfate, trimethyl phosphate, and iodomethane.

In preferred embodiments of the present invention, said solvent is selected from the group consisting of branched and linear $C_1$ to $C_4$ alkanols.

Suitable examples of the solvent include lower alkanols such as methanol, ethanol, 2-propanol, 1-propanol and tert-butanol; or dimethyl sulfoxide, N,N-dimethylformamide, N,N-dimethylacetamide and 1-methyl-2-pyrrolidinone.

Preferably, the polar solvent is methanol at using calcium oxide (or methoxide) as base and 1-propanol at using magnesium alkoxide or barium oxide as base.

The amount of the reaction solvent is preferably more than 7 ml, and more preferably from 10 to 15 ml to one gram of ICA.

The reaction is normally carried out under reflux.

The presence of moisture in the reaction mixture during the alkylation reaction can cause a decrease in the regioselectivity. However, in the process described in this invention, the solvent employed does not have to be anhydrous because the alkaline earth metal oxide or alkoxide effects drying of the solvent as well as being the base in the reaction. Owing to the moisture sensitivity of the reaction mixture, it is best to carry out the reaction in an inert atmosphere, usually under nitrogen.

Since the progress of the reaction can be monitored by use of high performance liquid chromatography, the reaction may be stopped after the disappearance of the starting material.

In this process, 1-MICA ester, 2-MICA ester and ICA ester are obtained in amounts less than 0.1%.

On an initial stage of the process, a mixture of oxide or alkoxide and non-anhydrous solvent is heated under reflux under a nitrogen atmosphere to dry the solvent. Preferable period of the reflux is two hours.

On a following stage, ICA is added to the mixture of the oxide or alkoxide and the solvent, and the reaction mixture is heated under reflux to obtain dianion of ICA. Preferable period of the reflux is two hours (the reaction mixture is a suspension).

On a final stage, a methylating agent is added dropwise to the dianion of ICA under reflux during two hours and the reflux is continued. The subsequent reaction time with the methylating agent depends on its reactivity. Preferably, the reaction time is 3–4 hours when dimethyl sulfate is used.

In the end of the reaction, water and base (aqueous solution of sodium hydroxide, potassium hydroxide and the like) are added to produce pH of about 14 and to hydrolyze the excess of the methylating agent. Then, an acid (hydrochloric acid, sulfuric acid and the like) is added to produce pH of about 4 and to decompose the alkaline earth metal salt of 1-MICA. In cases of using calcium and barium oxides (or alkoxides), calcium (or barium) sulfate is collected by filtration and the solvent is removed under reduced pressure from the filtrate. The residuary mixture is then stirred vigorously with a control of pH at about 4 for six hours to carry out an optimal precipitation of crude 1-MICA. The crude 1-MICA is treated by slurrying it in alkanol-water mixture with heating under reflux. The solid precipitate is collected by filtration to give pure 1-MICA.

According to the present invention, 1-methylindazole-3-carboxylic acid (I) can be obtained in high yield from ICA by using the oxide or alkoxide of the alkaline earth metal as base via a simple procedure.

The process of the present invention can be utilized for producing Granisetron or a salt thereof. In a preferred embodiment, the present invention provides a process for producing Granisetron, which process comprises reacting an indazole-3-carboxylic acid of formula (VI):

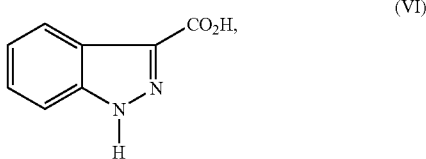

(VI)

with a methylating agent in the presence of an alkaline earth metal oxide or alkoxide in an appropriate solvent, to produce a 1-methylindazole-3-carboxylic acid of formula (I):

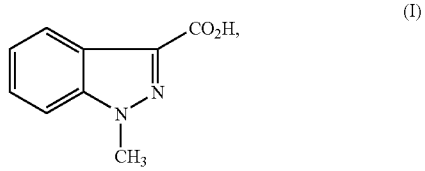

(I)

and converting the compound of formula (I) into a compound of the formula (VII):

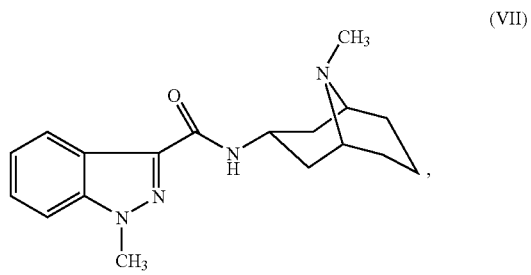

(VII)

to produce Granisetron, and, optionally, forming a salt of Granisetron.

The conversion of formula (I) into Granisetron can be performed using any suitable synthetic process, including, for example, coupling a compound of formula (I) with a suitable amine, to produce Granisetron. For example, a compound of formula (I) can be coupled with endo-9-methyl-9-azabicyclo[3.3.1]nonane-3-amine of the formula (VIII):

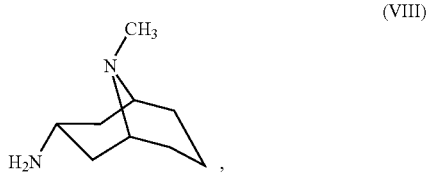

(VIII)

or a suitable derivative or precursor thereof, to produce Granisetron. In a preferred embodiment, the method of the present invention includes coupling the compound of formula (I) with the amine of formula (VIII), to produce Granisetron, and, optionally forming a salt of Granisetron, which is preferably Granisetron hydrochloride.

Coupling the compound of formula (I) with a suitable amine can be performed using known synthetic reactions, which are used in the formation of amide bonds. In one embodiment, the coupling includes converting a compound of formula (I) into a intermediate of the formula (IA):

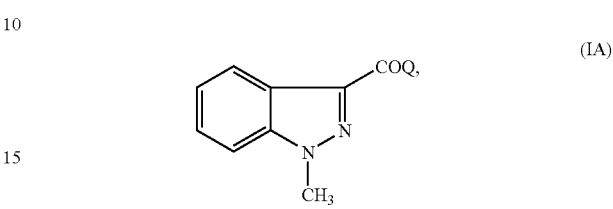

(IA)

wherein Q is a substituent displaceable by a nucleophile, and reacting the intermediate of formula (IA) with a suitable amine, e.g., endo-9-methyl-9-azabicyclo[3.3.1]nonane-3-amine, to produce Granisetron.

Suitable intermediates of formula (IA) can include, for example, acid halides (wherein Q is a halogen, e.g., chloride), mixed anhydrides that promote amide bond formation (e.g., wherein Q is an alkoxycarboxylate, e.g., isobutoxycarbonyloxy), activated esters that promote amide bond formation (e.g., wherein Q is benzotriazolyloxy), catalytic tertiary amine intermediates that promote amide bond formation (e.g., wherein Q is 4-dimethylaminopyridinium), and the like. Exemplary coupling methods are described, for example, in EP 0200444 A1 and EP 0200444 B1.

In accordance with the present invention, Granisetron can be produced in the form of a salt or the free base. It will be appreciated that reactants, reagents and reaction conditions can be chosen such that Granisetron is produced in the form of a salt or the free base. For example, reacting the intermediate of formula (IA), wherein Q is chloride, with endo-9-methyl-9-azabicyclo[3.3.1]nonane-3-amine in the absence of a base can produce Granisetron in the form of a hydrochloride salt. Reacting the intermediate of formula (IA), wherein Q is chloride, with endo-9-methyl-9-azabicyclo[3.3.1]nonane-3-amine in the presence of a suitable base, or isolating the product under basic conditions, can produce Granisetron in the form of a free base.

It will also be appreciated that methods for converting Granisetron from a free base into a salt, e.g., an acid addition salt, are well known in the art. For instance, Granisetron can be converted from a free base into the hydrochloride salt by reacting Granisetron free base with HCl. Methods for converting Granisetron from a salt into the free base also are well known in the art. For instance, Granisetron can be converted from the hydrochloride salt into the free base by reacting Granisetron hydrochloride with a suitable base, e.g., $NaHCO_3$.

The present invention will be concretely illustrated by Examples, which show the method for preparation of the compound of formula (I).

While the invention will now be described in connection with certain preferred embodiments in the all alternatives, modifications and equivalents following examples so that aspects thereof may be more fully understood and appreciated, it is not intended to limit the invention to these particular embodiments. On the contrary, it is intended to cover as may be included within the scope of the invention as defined by the appended claims. Thus, the following examples which include preferred embodiments will serve to illustrate the practice of this invention, it being understood that the particulars are shown by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

Preparation of 1-MICA by Reaction of ICA with Dimethyl Sulfate in Methanol in the Presence of Calcium Oxide Calcium oxide (7.0 g, 0.124 mole, 2.0 molar equiv.) was added to technical methanol (150 ml) and the mixture was heated under reflux for 2 hours in a nitrogen atmosphere. Indazole-3-carboxylic acid (10 g, 0.062 mole) was then added and the reflux was continued for 2 hours. Dimethyl sulfate (15.6 g, 11.8 ml, 0.124 mole, 2.0 molar equiv.) was added dropwise under reflux for 2 hours and the reflux was continued for a further 2 hours (the composition of the reaction mixture by HPLC was: 96.49% 1-MICA, 0.75% 2-MICA, and 2.76% ICA). Water (100 ml) and 46% aqueous sodium hydroxide solution were added to produce pH of about 14. Then, conc. hydrochloric acid was added to the reaction mixture to produce pH of about 4. Calcium sulfate was collected by filtration and washed on filter with hot methanol (3×30 ml). The methanol was removed under reduced pressure from the filtrate. The residuary mixture was stirred vigorously for 6 hours with a control pH of about 4. The solid product was collected by filtration, washed with water (3×30 ml), and dried in oven at 50° C. overnight to give crude 1-MICA (10.4 g, 95.8% yield, purity by HPLC: 99.0%). The crude 1-MICA (10.4 g) was treated by slurry in methanol-water (3:7) mixture at heating under reflux for 4 hours. The suspension was cooled to room temperature and the solid product was collected by filtration, washed with methanol-water (3:7) mixture (3×10 ml), and dried in oven at 50° C. overnight to give pure 1-MICA (9.3 g, 85.6% yield, purity by HPLC: 99.70%).

EXAMPLE 2

Preparation of 1-MICA by Reaction of ICA with Iodomethane in Methanol in the PRESENCE of Calcium Oxide Calcium oxide (7.0 g, 0.124 mole, 2 molar equiv.) was added to technical methanol (150 ml) under nitrogen atmosphere and the mixture was heated under reflux for 2 hours. Indazole-3-carboxylic acid (10 g, 0.062 mole) was then added and the mixture was heated under reflux for 2 hours. Iodomethane (26.3 g, 11.55 ml, 0.185 mole, 3 equiv.) in methanol (20 ml) was then added dropwise under reflux for 2 hours and the reflux was continued for a further 24 hours (the composition of the reaction mixture by HPLC was: 95.07% 1-MICA, 0.46% 2-MICA, and 4.47% ICA). The mixture was kept at room temperature overnight (the composition of the reaction mixture by HPLC was: 98.87% 1-MICA, 0.50% 2-MICA, and 0.63% ICA). Water (100 ml) and conc. hydrochloric acid were added to the mixture to produce pH of about 4. The mixture was filtered and the methanol was removed under reduced pressure from the filtrate. The residuary suspension was stirred vigorously for 6 hours with a control of pH of about 4. The solid product was collected by filtration, washed with water (3×30 ml), and dried in oven at 50° C. overnight to obtain crude 1-MICA (10.8 g, 99% yield, purity by HPLC: 99.82%). The crude 1-MICA was treated by slurry in water (50 ml) at room temperature for 4 hours. The solid product was collected by filtration, washed with water (3×30 ml), and dried oven at 50° C. overnight to give pure 1-MICA (9.1 g, 83.8% yield, purity by HPLC: 99.91%).

EXAMPLE 3

Preparation of 1-MICA by Reaction of ICA with Dimethyl Sulfate in 1-Propanol in the Presence of Barium Oxide Barium oxide (19 g, 0.124 mole, 2 molar equiv.) was added to technical 1-propanol (150 ml) under nitrogen atmosphere and the mixture was heated under reflux for 2 hours. Indazole-3-carboxylic acid (10 g, 0.062 mole) was then added and the mixture was heated under reflux for 2 hours. Dimethyl sulfate (15.6 g, 11.8 ml, 0.124 mole, 2 molar equiv.) was added dropwise under reflux for 2 hours (the composition of the reaction mixture by HPLC was: 99.14% 1-MICA, 0.16% 2-MICA, and 0.71% ICA). The mixture was kept at room temperature overnight (the composition of the reaction mixture by HPLC was: 99.28% 1-MICA, 0.15% 2-MICA, and 0.56% ICA). Water (100 ml) and 46% aqueous sodium hydroxide solution were added to the mixture to produce pH of about 14. Then, 20% aqueous sulfuric acid was added to produce pH of about 4, barium sulfate was collected by filtration and washed on filter with hot 1-propanol (3×30 ml). The 1-propanol was removed under reduced pressure from the filtrate and the residuary mixture was stirred vigorously for 6 hours with a control of the pH of about 4. The solid product was collected by filtration, washed with water (3×30 ml) and dried in oven at 50% C overnight to yield crude 1-MICA (8.7 g, 80.1% yield, purity by HPLC: 99.50%). The crude 1-MICA was treated by slurry in methanol-water (3:7) mixture (30 ml) at heating under reflux for 4 hours. The precipitate was collected by filtration after cooling the mixture to room temperature, washed with methanol-water (3:7) mixture (3×10 ml) and dried in oven at 50° C. overnight to give pure 1-MICA (7.1 g, 65.4% yield, purity by HPLC: 99.88%).

EXAMPLE 4

Preparation of 1-MICA by Reaction of ICA with Dimethyl Sulfate in Methanol in the Presence of Calcium Methoxide Calcium methoxide (13.0 g, 0.124 mole, 2 molar equiv.) was added to technical methanol (150 ml) under nitrogen atmosphere and the mixture was heated under reflux for 2 hours. Indazole-3-carboxylic acid (10 g, 0.062 mole) was then added and the mixture was heated under reflux for 2 hours. Dimethyl sulfate (15.6 g, 11.8 ml, 0.124 mole, 2 molar equiv.) was added dropwise under reflux for 2 hours and the reflux was continued for a further 1 hour (the composition of the reaction mixture by HPLC was: 98.88% 1-MICA, 0.54% 2-MICA, and 0.57% ICA). The mixture was kept at room temperature overnight (the composition of the reaction mixture by HPLC was: 98.92% 1-MICA, 0.58% 2-MICA, and 0.4% ICA). Water (100 ml) and 46% aqueous sodium hydroxide solution were added to the reaction mixture to produce pH of about 14. Then, conc. hydrochloric acid was added to the reaction mixture to produce pH of about 4. Calcium sulfate was collected by filtration and washed on filter with hot methanol (3×30 ml). The methanol was removed under reduced pressure from the filtrate. Conc. hydrochloric acid was added to produce pH of about 1 and the mixture was stirred vigorously for 2 hours. The solid product was collected by filtration, washed with 5% hydrochloric acid (3×30 ml), and dried in oven at 50° C. overnight to give 1-MICA hydrochloride (11.5 g, 87.7% yield, purity by HPLC: 99.19%).

EXAMPLE 5

Preparation of 1-MICA by Reaction of ICA with Dimethyl Sulfate in 1-Propanol in the Presence of Magnesium Ethoxide Magnesium ethoxide (14.10 g, 0.124 mole, 2 molar equiv.) was added to technical 1-propanol (100 ml) under nitrogen atmosphere and the mixture was heated under reflux for 2 hours. Indazole-3-carboxylic acid (10 g, 0.0617 mole) was then added and the reflux was continued for a further 2 hours. Dimethyl sulfate (13.3 g, 10 ml, 0.105 mole, 1.7 molar equiv.) was added dropwise under reflux for 2 hours to the suspension and the reflux was continued for a further 2 hours (the composition of the reaction mixture by HPLC was: 96.03% 1-MICA, 1.50% 2-MICA, and 2.50% ICA). The mixture was kept at room temperature overnight (the composition of the reaction mixture by HPLC was: 97.52% 1-MICA, 1.44% 2-MICA, and 1.04% ICA). Water (100 ml) and 46% aqueous sodium hydroxide solution were added to the mixture to produce pH of about 14. Then, conc. hydrochloric acid was added to the suspension to produce pH of about 4 and obtain a solution. The 1-propanol removed under reduced pressure from the solution. The residuary mixture was stirred vigorously for 6 hours with a control of the pH of about 4. The solid product was collected by filtration, washed with water (3×15 ml), and dried in oven overnight at 50+C to yield crude 1-MICA (10.8 g, 99.4% yield, purity by HPLC: 99.3%). The crude 1-MICA (10.8 g) was treated by slurry in methanol-water (3:7) mixture (33 ml) at heating under reflux for 4 hours. The solid product was collected by filtration after cooling the mixture to room temperature, washed with methanol-water (3:7) mixture (3×10 ml), and dried in oven overnight at 50° C. to give pure 1-MICA (8.6 g, 79.2% yield, purity by HPLC: 99.87%).

EXAMPLE 6

Preparation of 1-MICA by Reaction of ICA with Trimethyl Phosphate in 1-Propanol in the Presence of Magnesium Ethoxide Magnesium ethoxide (14.10 g, 0.124 mole, 2 molar equiv.) was added to technical 1-propanol (100 ml) under nitrogen atmosphere and the mixture was heated under reflux for 2 hour. Indazole-3-carboxylic acid (10 g, 0.0617 mole) was then added and the reflux was continued for 2 hours. Trimethyl phosphate (14.7 g, 12.3 ml, 0.105 mole, 1.7 molar equiv.) was added dropwise under reflux for 2 hours and the reflux was continued for a further 5 hours (the composition of the reaction mixture by HPLC was: 95.61% 1-MICA, 1.89% 2-MICA, and 2.50% ICA). The mixture was kept at room temperature overnight (the composition of the reaction mixture by HPLC was: 97.24% 1-MICA, 2.17% 2-MICA, and 0.58% ICA). Water (100 ml) and 46% aqueous sodium hydroxide solution were added to the reaction mixture to produce pH of about 14. Then, conc. hydrochloric acid was added to the suspension to produce pH of about 4 and obtain a solution. The propanol was removed under reduced pressure from the solution. The residuary mixture was stirred vigorously for 6 hours with a control of the pH of about 4. The solid product was collected by filtration, washed with water (3×30 ml), and dried in oven at 50° C. overnight to give crude 1-MICA (10.1 g, 93.0% yield, purity by HPLC: 99.24%). The crude 1-MICA (10.1 g) was treated by slurry in methanol-water (3:7) mixture (31 ml) at heating under reflux for 4 hours. The solid product was collected by filtration, washed with methanol-water (3:7) mixture (3×10 ml), and dried in oven at 50° C. to obtain pure 1-MICA (8.5 g, 78.3% yield, purity by HPLC: 99.78%).

EXAMPLE 7

Preparation of 1-MICA by Reaction of ICA with Dimethyl Sulfate in 1-Propanol in the Presence of Magnesium Propoxide Obtained In Situ from Magnesium Metal Magnesium (3 g, 0.123 mole, 2 molar equiv.) was added to technical 1-propanol (100 ml) and the mixture was heated to reflux under nitrogen atmosphere. Then, sublimed iodine (0.2 g) as catalyst was added and the reflux was continued for 4 hours to obtain magnesium propoxide. Indazole-3-carboxylic acid (10 g, 0.0617 mole) was then added and the reflux was continued for 2 hours. Dimethyl sulfate (13.3 g, 10 ml, 0.105 mole, 1.7 molar equiv.) was added dropwise under reflux for 2 hours and the reflux was continued for a further 3 hours (the composition of the reaction mixture by HPLC was: 97.09% 1-MICA, 0.37% 2-MICA, and 2.54% ICA). The mixture was kept at room temperature overnight (the composition of the reaction mixture by HPLC was: 97.61% 1-MICA, 0.19% 2-MICA, and 2.21% ICA). Water (100 ml) and 46% aqueous sodium hydroxide solution were added to the reaction mixture to produce-pH of about 14. Then, conc. hydrochloric acid was added to the suspension to produce pH of about 4 and obtain a solution. The 1-propanol was removed under reduced pressure from the solution. The residuary mixture was stirred for 6 hours with a control of pH of about 4. The solid product was collected by filtration, washed with water (3×30 ml), and dried in oven at 50° C. overnight to give crude 1-MICA (10.2 g, 93.9% yield, purity by HPLC: 98.73%). The crude compound (10.2 g) was treated by slurry at heating under reflux in methanol-water (3:7) mixture (31 ml) for 4 hours. The precipitate was collected by filtration after cooling the mixture to room temperature, washed with methanol-water (3:7) mixture (3×10 ml), and dried in oven at 50° C. overnight to prepare pure 1-MICA (9.1 g, 83.8% yield, purity by HPLC: 99.71%).

EXAMPLE 8

Preparation of Granisetron Hydrochloride—Reference Example

Following the example described in EP 200444, at pages 4–5, 1-MICA is converted to its corresponding acid chloride with thionyl chloride using conventional methods.

A stirred solution of 1-methylindazole-3-carboxylic acid chloride in dichloromethane is treated with a solution of endo-9-methyl-9-azabicyclo[3.3.1]nonane-3-amine and triethylamine in dichloromethane. After 2 hours, the reaction is washed with saturated aq. $NaHCO_3$ and dried. The product remaining after evaporation is purified by column chromatography (TLC-alumina, chloroform) and treated with hydrogen chloride to give the title compound.

All references, including publications, patent applications, and patents, cited herein are hereby incorporated by reference to the same extent as if each reference were individually and specifically indicated to be incorporated by reference and were set forth in its entirety herein. It will be evident to those skilled in the art that the invention is not limited to the details of the foregoing illustrative examples and that the present invention may be embodied in other specific forms without departing from the essential attributes thereof, and it is therefore desired that the present embodiments and examples be considered in all respects as illustrative and not restrictive, reference being made to the appended claims, rather than to the foregoing description, and all changes which come within the meaning and range of equivalency of the claims are therefore intended to be embraced therein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A process for producing Granisetron, which process comprises reacting an indazole-3-carboxylic acid of formula (VI):

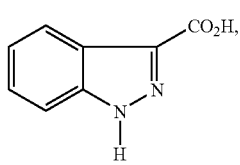

with a methylating agent in the presence of an alkaline earth metal oxide in a solvent, to produce a 1-methylindazole-3-carboxylic acid of formula (I):

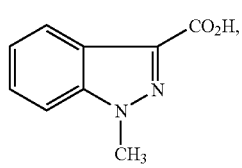

converting the compound of formula (I) into a compound of the formula (VII):

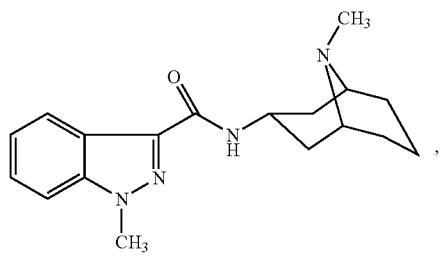

to produce Granisetron, and, optionally, forming a salt of Granisetron.

2. The method of claim 1, comprising coupling the compound of formula (I) with an amine, to produce Granisetron.

3. The method of claim 2, wherein the amine is endo-9-methyl-9-azabicyclo[3.3.1]nonane-3-amine of the formula (VIII):

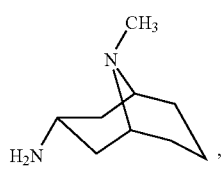

or a derivative or a precursor thereof.

4. The method of claim 2, comprising converting the compound of formula (I) into a intermediate of the formula (IA):

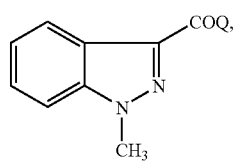

wherein Q is a substituent displaceable by a nucleophile, and reacting the intermediate of formula (IA) with an amine, to produce Granisetron.

5. The method of claim 4, wherein Q is a halogen.

6. The method of claim 4, wherein Q is chloride.

7. The method of claim 4, wherein the amine is endo-9-methyl-9-azabicyclo[3.3.1]nonane-3-amine of the formula (VIII):

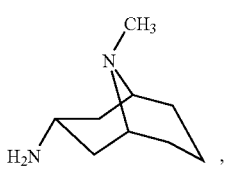

or a derivative or a precursor thereof.

8. The method of claim 1, comprising forming a salt of Granisetron.

9. The method of claim 8, wherein the salt is Granisetron hydrochloride.

* * * * *